US00PP29709P2

(12) United States Plant Patent
Lannes

(10) Patent No.: US PP29,709 P2
(45) Date of Patent: Sep. 25, 2018

(54) ***MANDEVILLA* PLANT NAMED 'LANOKLAHOMA'**

(50) Latin Name: *Mandevilla sanderi*
Varietal Denomination: Lanoklahoma

(71) Applicant: Robert Lannes, Malause (FR)

(72) Inventor: Robert Lannes, Malause (FR)

(73) Assignee: D.H.M. Innovation S.A.S., Malause (FR)

( * ) Notice: Subject to any disclaimer, the term of this patent is extended or adjusted under 35 U.S.C. 154(b) by 0 days.

(21) Appl. No.: 15/731,679

(22) Filed: Jul. 15, 2017

(51) Int. Cl.
*A01H 5/02* (2018.01)

(52) U.S. Cl.
USPC ..... Plt./232

(58) Field of Classification Search
USPC ..... Plt./232
See application file for complete search history.

*Primary Examiner* — Annette H Para
(74) *Attorney, Agent, or Firm* — C. A. Whealy

(57) ABSTRACT

A new and distinct cultivar of *Mandevilla* plant named 'Lanoklahoma', characterized by its upright and twining plant habit; moderately vigorous growth habit; glossy dark green-colored leaves; freely flowering habit; and light red-colored flowers that are flushed with yellow orange.

2 Drawing Sheets

Botanical designation: *Mandevilla sanderi.*
Cultivar denomination: 'LANOKLAHOMA'.

BACKGROUND OF THE INVENTION

The present invention relates to a new and distinct cultivar of *Mandevilla* plant, botanically known as *Mandevilla sanderi* and hereinafter referred to by the name 'Lanoklahoma'.

The new *Mandevilla* plant is a product of a planned breeding program conducted by the Inventor in Malause, France. The objective of the breeding program is to create new *Mandevilla* plants with good plant habit and numerous attractive flowers.

The new *Mandevilla* plant originated from a cross-pollination conducted by the Inventor in Malause, France in June, 2015 of a proprietary selection of *Mandevilla sanderi* identified as code number SI 07-232-060-EF, not patented, as the female, or seed, parent with a proprietary selection of *Mandevilla sanderi* identified as code number SI 10-303-001, not patented, as the male, or pollen, parent. The new *Mandevilla* plant was discovered and selected by the Inventor as a single flowering plant from within the progeny of the stated cross-pollination in a controlled greenhouse environment in Malause, France in July, 2016.

Asexual reproduction of the new *Mandevilla* plant by cuttings in a controlled greenhouse environment in Malause, France, since September, 2016 has shown that the unique features of this new *Mandevilla* plant are stable and reproduced true to type in successive generations.

SUMMARY OF THE INVENTION

Plants of the new *Mandevilla* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Lanoklahoma'. These characteristics in combination distinguish 'Lanoklahoma' as a new and distinct *Mandevilla* plant:

1. Upright and twining plant habit.
2. Moderately vigorous growth habit.
3. Glossy dark green-colored leaves.
4. Freely flowering habit.
5. Light red-colored flowers that are flushed with yellow orange.

Plants of the new *Mandevilla* can be compared to plants of the female parent selection. Plants of the new *Mandevilla* differ primarily from plants of the female parent selection in the following characteristics:

1. Flowers of plants of the new *Mandevilla* are arranged in inflorescences whereas plants of the female parent selection have single flowers.
2. Plants of the new *Mandevilla* have smaller flowers than plants of the female parent selection.
3. Plants of the new *Mandevilla* and the female parent selection differ in flower color as plants of the female parent selection have rose-colored flowers.

Plants of the new *Mandevilla* can be compared to plants of the male parent selection. Plants of the new *Mandevilla* differ primarily from plants of the male parent selection in the following characteristics:

1. Plants of the new *Mandevilla* flower earlier than plants of the male parent selection.
2. Plants of the new *Mandevilla* have larger flowers than plants of the male parent selection.
3. Plants of the new *Mandevilla* and the male parent selection differ in flower color as plants of the male parent selection have scarlet-colored flowers.

Plants of the new *Mandevilla* can also be compared to plants of *Mandevilla hybrida* 'Sunpapri', disclosed in U.S. Plant Pat. No. 28,277. In side-by-side comparisons, plants of the new *Mandevilla* differ primarily from plants 'Sunpapri' in the following characteristics:

1. Plants of the new *Mandevilla* have smaller leaves than plants of 'Sunpapri'.
2. Plants of the new *Mandevilla* have smaller flowers than plants of 'Sunpapri'.

3. Plants of the new *Mandevilla* and 'Sunpapri' differ in flower color as plants of 'Sunpapri' have pale orange-colored flowers.
4. Flower color of plants of the new *Mandevilla* does not fade under high light or high temperatures conditions whereas flower color of plants of 'Sunpapri' fades under high light and high temperature conditions.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph on the first sheet comprises a side perspective view of a typical flowering plant of 'Lanoklahoma' grown in a container.

The photograph on the second sheet is a close-up view of typical open flowers and flower buds of 'Lanoklahoma'.

DETAILED BOTANICAL DESCRIPTION

The aforementioned photographs and following observations, measurements and values describe plants grown during the late spring and early summer in 17-cm containers in polyethylene-covered greenhouse in Malause, France and under cultural practices typical of commercial *Mandevilla* production. During the production of the plants, day temperatures ranged from 15° C. to 26° C. and night temperatures ranged from 14° C. to 15° C. Plants were nine months old when the photographs and description were taken. In the following description, color references are made to The Royal Horticultural Society Colour Chart, 2015 Edition, except where general terms of ordinary dictionary significance are used.

Botanical classification: *Mandevilla* x *amabilis* X *Mandevilla hybrida* 'Lanoklahoma'.

Parentage:

*Female, or seed, parent*.—Proprietary selection of *Mandevilla sanderi* identified as code number SI 07-232-060-EF, not patented.

*Male, or pollen, parent*.—Proprietary selection of *Mandevilla sanderi* identified as code number SI 10-303-001, not patented.

Propagation:

*Type*.—By vegetative cuttings.

*Time to initiate roots, summer*.—About four weeks at temperatures about 18° C. to 30° C.

*Time to initiate roots, winter*.—About five weeks at temperatures about 16° C. to 25° C.

*Time to produce a rooted young plant, summer*.—About ten weeks at temperatures about 18° C. to 30° C.

*Time to produce a rooted young plant, winter*.—About twelve weeks at temperatures about 16° C. to 25° C.

*Root description*.—Fibrous, fine; typically light yellowish white in color, actual color of the roots is dependent on substrate composition, water quality, fertilizers, substrate temperature and physiological age of roots.

*Rooting habit*.—Freely branching; medium density.

Plant description:

*Plant and growth habit*.—Upright and twining plant habit; overall plant shape is broadly oblong; moderately vigorous growth habit.

*Plant height, soil level to top of foliar plane*.—About 57.4 cm.

*Plant height, soil level to top of floral plane*.—About 49.4 cm.

*Plant diameter* (*spread*).—About 26.9 cm.

*Lateral branch description*.—Branching habit: Moderately freely branching habit with about three primary lateral branches, each with about two secondary lateral branches developing per plant. Length: About 49.2 cm. Diameter: About 3 mm. Internode length: About 5.6 cm. Strength: Strong. Texture and luster: Smooth, glabrous; glossy; with development, woody. Color, developing: Close to 144A; at the internodes, close to 144A to 144B. Color, developed: Close to 144A to 144B tinged with close to 173A to 173B; color becoming closer to N199C if woody.

Leaf description:

*Arrangement*.—Opposite, simple.

*Length*.—About 7.4 cm.

*Width*.—About 3.8 cm.

*Shape*.—Oblong to obovate.

*Apex*.—Short apiculate.

*Base*.—Truncate.

*Margin*.—Entire.

*Texture and luster, upper surface*.—Smooth, glabrous; glossy.

*Texture and luster, lower surface*.—Smooth, glabrous; moderately glossy.

*Venation pattern*.—Pinnate.

*Color*.—Developing leaves, upper surface: Slightly darker than 143A. Developing leaves, lower surface: Close to between 138A and 147B. Full expanded leaves, upper surface: Darker than between NN137A and 147A; venation, close to 143B. Fully expanded leaves, lower surface: Close to 146A; venation, close to 144B.

*Petioles*.—Length: About 6 mm. Diameter: About 2 mm by 2.5 mm. Strength: Moderately strong. Texture and luster, upper and lower surfaces: Smooth, glabrous; glossy. Color, upper surface: Close to 144A to 144B. Color, lower surface: Close to 145B.

Flower description:

*Flower type and flowering habit*.—Single salverform flowers arranged in axillary cymes; flowers star-shaped and face mostly upright and outwardly; freely flowering habit with about 15 flowers developing per inflorescence and about 15 open flowers and about 90 flower buds develop per plant.

*Natural flowering season*.—Plants flower continuously from spring into the autumn in France.

*Flower longevity on the plant*.—About 15 days; flowers not persistent.

*Fragrance*.—None detected.

*Inflorescence height*.—About 17.3 cm.

*Inflorescence diameter*.—About 9.9 cm.

*Flower buds*.—Length: About 3.9 cm. Diameter: About 6 mm. Shape: Narrowly oblanceolate. Texture and luster: Smooth, glabrous; slightly glossy. Color: Close to 18A; towards the base, close to 151D; tube, close to 144C.

*Flowers*.—Appearance: Flared trumpet, corolla fused and five-parted. Diameter: About 6 cm. Depth (length): About 3.7 cm. Throat diameter: About 5 mm. Tube length: About 2 cm. Tube diameter, mid-section: Close to 3.5 mm.

*Corolla*.—Quantity and arrangement: Five petals arranged in a single whorl and fused towards the base forming a funnel-shaped tube. Petal length: About 4.9 cm. Petal width: About 2.1 cm. Petal shape and appearance: Roughly spatulate; lower 45% of the petal is fused into a tube. Petal apex: Acute. Petal margin: Entire; slightly undulate. Petal texture and luster, upper surface: Smooth, glabrous; velvety; matte. Petal texture and luster, lower surface: Smooth, glabrous; slightly velvety; slightly glossy. Throat texture: Smooth, glabrous; moderately velvety. Tube texture: Smooth, glabrous; slightly velvety. Color: Petal, when opening, upper surface: Close to 31A; towards the base, flushed with close to 20A. Petal, when opening, lower surface: Close to 25C; midvein, close to 13B. Petal, fully opened, upper surface: Close to 41A flushed with close to 21B; venation, close to 41A flushed with close to 21B; color becoming closer to 47C with development. Petal, fully opened, lower surface: Close to 39B; venation, close to 11B; color becoming closer to 48C with development. Throat: Close to 15B; venation, close to 23A. Tube: Close to 145B; venation, close to 145B.

*Corona*.—Quantity and arrangement: Five sepals arranged in a single whorl. Calyx length: About 6 mm. Calyx diameter: About 5 mm. Sepal length: About 6 mm. Sepal width: About 1 mm. Sepal shape: Narrowly deltoid. Sepal apex: Narrowly acute. Sepal base: Broadly cuneate. Sepal margin: Entire. Sepal texture and luster, upper surface: Smooth, glabrous; glossy. Sepal texture and luster, lower surface: Smooth, glabrous; matte. Sepal color: When opening, upper and lower surfaces: Close to 152D; towards the apex, close to 180B. Fully opened, upper and lower surfaces: Close to 145B; towards the apex, close to 180B. Fully opened, lower surface: Close to 145A.

*Peduncles*.—Length: About 21.8 cm. Diameter: About 3 mm. Strength: Strong. Aspect: About 25° from vertical. Texture and luster: Smooth, glabrous; slightly glossy. Color: Close to 146C tinged with close to 179A.

*Pedicels*.—Length: About 2.2 cm. Diameter: About 2 mm. Strength: Strong. Aspect: About 25° from peduncle axis. Texture and luster: Smooth, glabrous; glossy. Color: Close to 145B to 145C tinged with close to 180C.

*Reproductive organs*.—Stamens: Quantity and arrangement: Typically five; basifixed; anthers connivent. Filament length: About 1 mm. Filament color: Close to 153C. Anther shape: Narrowly oblong. Anther length: About 6 mm. Anther diameter: About 1.25 mm. Anther color: Close to 162C. Pollen amount: None observed. Pistils: Quantity: Typically one. Pistil length: About 2 cm. Style length: About 1.8 cm. Style color: Close to 150C. Stigma diameter: About 1.5 mm. Stigma shape: Club-shaped. Stigma color: Close to 152C. Ovary color: Close to 144A.

*Seeds and fruits*.—Seed and fruit production have not been observed on plants of the new *Mandevilla* to date.

Disease & pest resistance: Plants of the new *Mandevilla* have not been noted to be resistant to pathogens and pests common to *Mandevilla* plants.

Temperature tolerance: Plants of the new *Mandevilla* have been observed to tolerate high temperatures of about 40° C. and to be suitable for USDA Hardiness Zones 9 through 13.

It is claimed:

1. A new and distinct *Mandevilla* plant named 'Lanoklahoma' as illustrated and described.

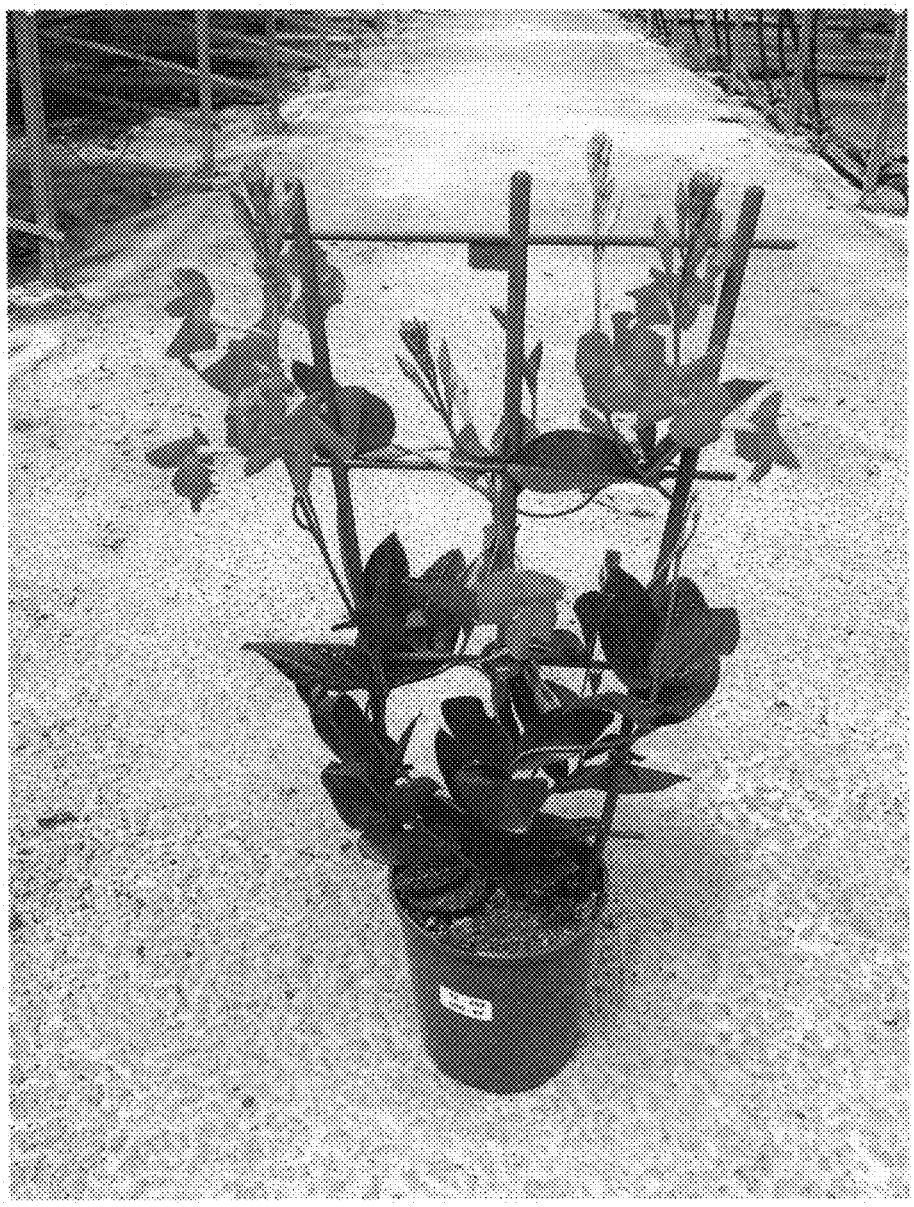

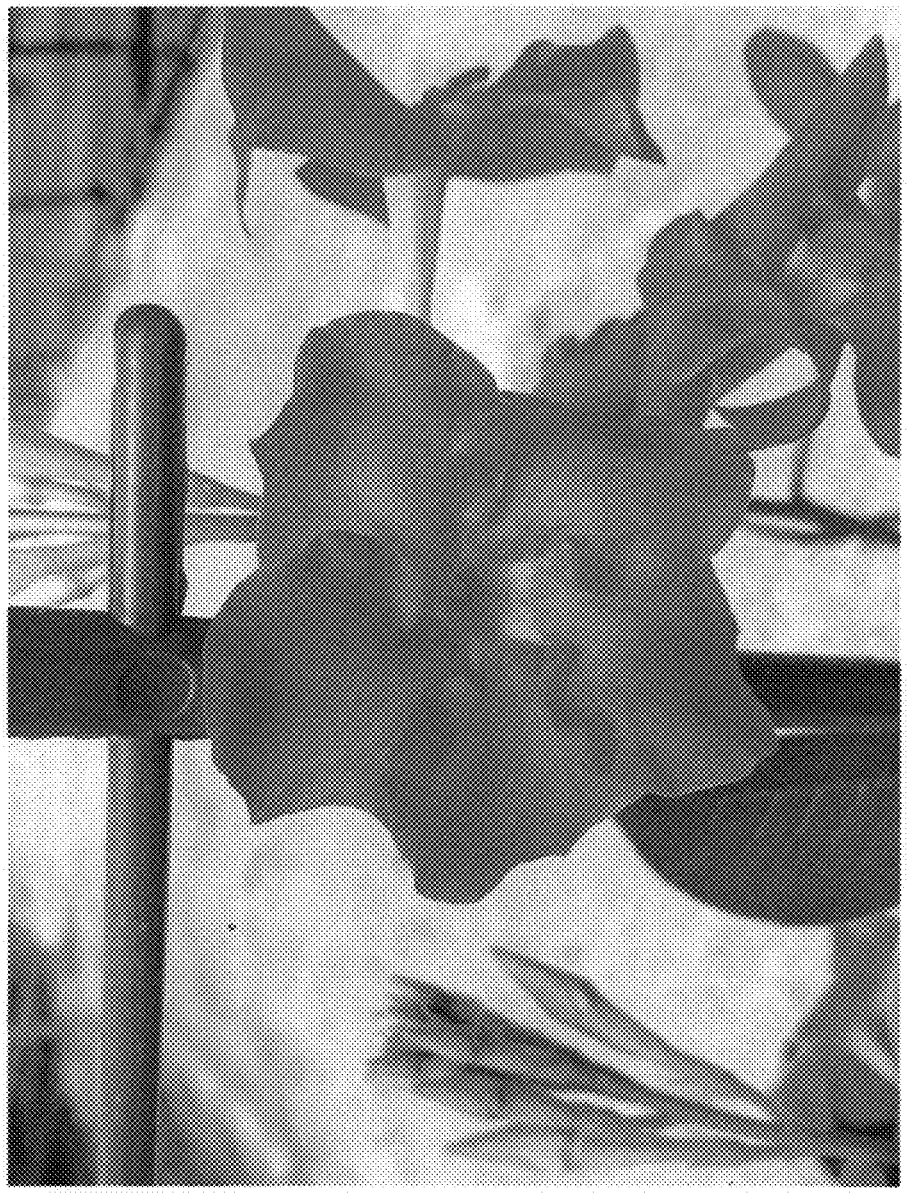

* * * * *